(12) United States Patent
Sidawi

(10) Patent No.: US 9,238,086 B2
(45) Date of Patent: Jan. 19, 2016

(54) SPILL-RESISTANT AIR FRESHENER CANISTER

(71) Applicant: Silver Coast Inc., Milton (CA)

(72) Inventor: Rami Sidawi, Milton (CA)

(73) Assignee: SILVER COAST, INC., Milton, Ontario (CA)

( * ) Notice: Subject to any disclaimer, the term of this patent is extended or adjusted under 35 U.S.C. 154(b) by 0 days.

(21) Appl. No.: 14/055,880

(22) Filed: Oct. 16, 2013

(65) Prior Publication Data

US 2014/0103136 A1    Apr. 17, 2014

Related U.S. Application Data

(60) Provisional application No. 61/714,742, filed on Oct. 16, 2012.

(51) Int. Cl.
*A61L 9/12* (2006.01)
*A61L 9/03* (2006.01)

(52) U.S. Cl.
CPC ............... *A61L 9/127* (2013.01); *A61L 9/037* (2013.01); *A61L 2209/133* (2013.01)

(58) Field of Classification Search
CPC ............ A61L 9/122; A61L 9/127; A61L 9/12
USPC ..................................................... 239/34–60
See application file for complete search history.

(56) References Cited

U.S. PATENT DOCUMENTS

| | | | | |
|---|---|---|---|---|
| 2,166,969 A * | 7/1939 | Rooch | | 239/42 |
| 2,246,008 A * | 6/1941 | Rooch | | 239/42 |
| 2,586,179 A * | 2/1952 | Rooch | | 239/42 |
| 2,723,158 A * | 11/1955 | Molina | | 239/44 |
| 5,875,968 A * | 3/1999 | Miller et al. | | 239/44 |
| 6,553,712 B1 * | 4/2003 | Majerowski et al. | | 43/131 |
| 7,614,568 B2 * | 11/2009 | Joshi et al. | | 239/6 |
| 7,857,236 B2 * | 12/2010 | Zlotnik et al. | | 239/34 |
| 8,005,350 B2 * | 8/2011 | Zlotnik et al. | | 392/395 |
| 2007/0001024 A1 * | 1/2007 | Wold et al. | | 239/34 |

* cited by examiner

*Primary Examiner* — Len Tran
*Assistant Examiner* — Tuongminh Pham
(74) *Attorney, Agent, or Firm* — Durham Jones & Pinegar, P.C.

(57) ABSTRACT

The present invention provides a spill-resistant air freshener canister that includes: a supply vessel filled with aromatic liquid that has a threaded mouth sealed with a puncturable foil/polyethylene membrane; a cylindrical inner sleeve incorporating a socket that sealably engages the threaded mouth of the supply vessel, the sleeve also having a cylindrical axial aperture at the bottom of the socket, and at least one seepage aperture at the very bottom of the socket which enables liquid from inside the supply vessel to escape in a radially outward direction to the exterior of the cylindrical inner sleeve; a cylindrical wick surrounding the cylindrical inner sleeve; and an evaporator cage into which the cylindrical inner sleeve is inserted, the evaporator cage having a fully-enclosed bottom portion containing a central projecting blade that fits through the axial aperture at the bottom of the socket. The bottom portion is ultrasonically welded to the bottom of the cylindrical inner sleeve.

4 Claims, 8 Drawing Sheets

SPILL-RESISTANT AIR FRESHENER CANISTER

BACKGROUND OF THE INVENTION

1. Field of the Invention

The present invention relates, generally, to air freshener canisters having a central supply vessel containing an aromatic liquid that is surrounded by an evaporation chamber enclosing a generally cylindrical wick that is wetted by liquid escaping from the supply vessel. More particularly, the present invention relates to a spill-resistant air freshener canister that has no unabsorbed standing aromatic liquid outside the vessel, with all aromatic liquid that has seeped from the supply vessel being absorbed by the wick.

2. Description of the Prior Art

Aromatic fluid delivery devices, such as fragrance dispensers, have been known in the art for many decades. One example of a dispenser for volatile fluid is disclosed in three related U.S. Pat. Nos. 5,533,705; 5,816,846 and 6,105,916. The device provides a drive selectively using a large or small motor providing an air stream for generating vapor from a wick, ceramic wafers, or discs containing vaporizable deodorant. Socket assemblies provide a socket for a motor of larger dimensions and a socket for a motor of smaller dimensions. A frame for a cabinet composed of a separate back plate, a top member and a bottom member of a resilient plastic so that the top member and bottom member are snap-locked to the back plate and secured further by projections from the top and bottom members in slots in the back plate. The bottom member is a liquid tight tray capable of processing deodorants contained in wick-equipped bottles and cans, porous impregnated ceramic discs, and porous impregnated fiber wafers. There is a bottle holder snap-locked to the underside of the top member. A battery-blower assembly is snap-locked to the back plate. The battery poles are joined to the wires from the blower-motor by clips using solderless connections.

More recently as disclosed in U.S. Pat. No. 6,957,779 is a framed fluid delivery device that is made up of a fluid-delivery cartridge for the timed-release delivery of a fluid. The fluid delivery cartridge retained by a frame assembly uses a base portion for the delivery of fluid released from a cartridge. The base secures the fluid delivery cartridge within the frame assembly proximate the end when fluid is released. The fluid-delivery cartridge has a bottom, a top, and sides, and a dispersion pad positioned proximate the bottom of the fluid-delivery cartridge that at least partially surrounds the sides of the fluid-delivery cartridge. A generator that generates gas is used for powered discharge of volatile liquid from the storage cell that is part of the fluid delivery cartridge. While conventional dispensers have been readily utilized in numerous commercial markets, they have not been configured to automatically dispense a fluid at predetermined intervals. In particular, many conventional dispensers are manually or electromechanically actuated by depressing, for example, a cap, a button, or a trigger mechanism. Such manually, or electromechanically actuated dispensers are cumbersome and expensive inasmuch as they have many costly components.

A more recent trend has seen the proliferation of fragrance canisters which have a central fluid supply vessel surrounded by an evaporation chamber enclosing a wick. U.S. Pat. No. 6,283,461 to Ashok Joshi, et al. discloses a fluid delivery device including a container for holding a predetermined quantity of fluid, a gas generator for generating gas within the container, and a dispenser for cyclically dispensing fluid at predetermined intervals out of the container without cyclical actuation by a user. Although the Joshi, et al. device represents an improvement in the art, in that the cost of fragrance dispensers is substantially reduced, the device is still unnecessarily complex and relatively costly.

U.S. Pat. No. 8,005,350 to Arnold H. Zlotnik, et al. discloses an aromatic odor neutralizer that includes a vaporization chamber containing a wick with an end part immersed in fluid in a storage cup that is gravity fed from an airtight vessel by the use of air pathways exposed when the liquid level in the cup is reduced. The vaporization chamber is located in a dispenser housing with an internal passage between end walls and communicating with vents in the sides for aerodynamic airflow to efficiently absorb vapors from a vaporizer chamber. Once activated by puncturing a lower portion of the vessel, the Zlotnick, et al. device soon reaches an equilibrium condition characterized by the presence of standing aromatic fluid in the storage cup. This standing fluid is subject to spillage if the air canister is not handled with care.

SUMMARY OF THE INVENTION

The present invention provides a spill-resistant air freshener canister that includes the following components: a supply vessel filled with aromatic liquid that has a threaded mouth sealed with a puncturable membrane; a cylindrical inner sleeve incorporating a socket that sealably engages the threaded mouth of the supply vessel, the sleeve also having a cylindrical axial aperture at the bottom of the socket, and at least one seepage aperture at the very bottom of the socket which enables liquid from inside the supply vessel to escape in a radially outward direction to the exterior of the cylindrical sleeve; a cylindrical wick surrounding the cylindrical inner sleeve; and an evaporator cage into which the cylindrical sleeve is inserted, the evaporator cage having a fully-enclosed bottom portion containing a central projecting blade that fits through the axial aperture at the bottom of the socket. The bottom portion is ultrasonically welded to the bottom of the cylindrical inner sleeve, leaving no gap between the bottom of the inner sleeve and the bottom portion of the evaporator cage. When a filled supply vessel is screwed into the socket, the projecting blade slices through the puncturable membrane which allows aromatic liquid to escape outside the cylindrical sleeve and wet the cylindrical wick. The air freshener canister is spill resistant, as there is no unabsorbed standing aromatic liquid outside the vessel. All of the aromatic liquid is either within the supply vessel or absorbed by the wick.

PREFERRED EMBODIMENT OF THE INVENTION

Figure 1:
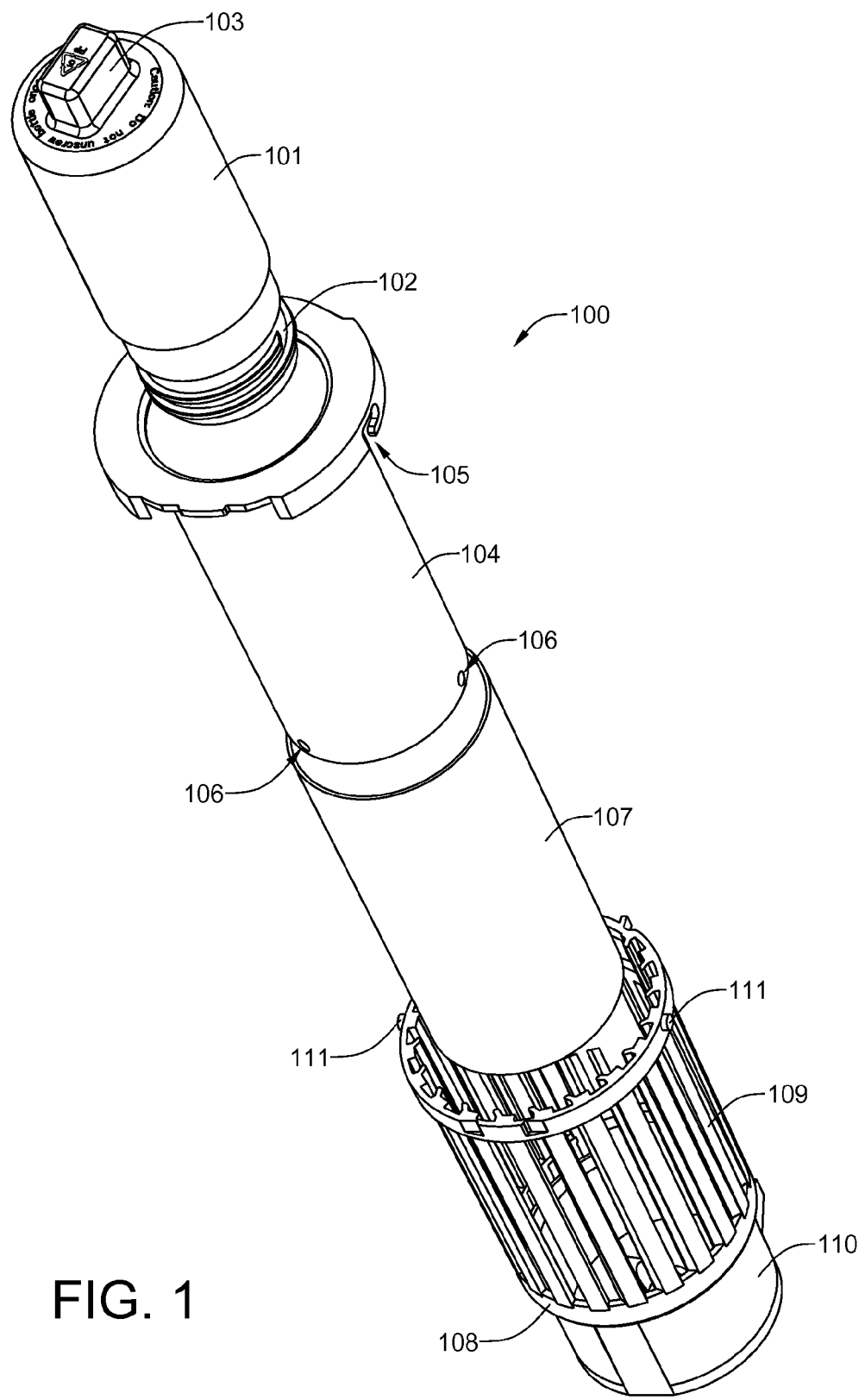
FIG. 1 is an exploded isometric view of the new air freshener canister.
Figure 2:
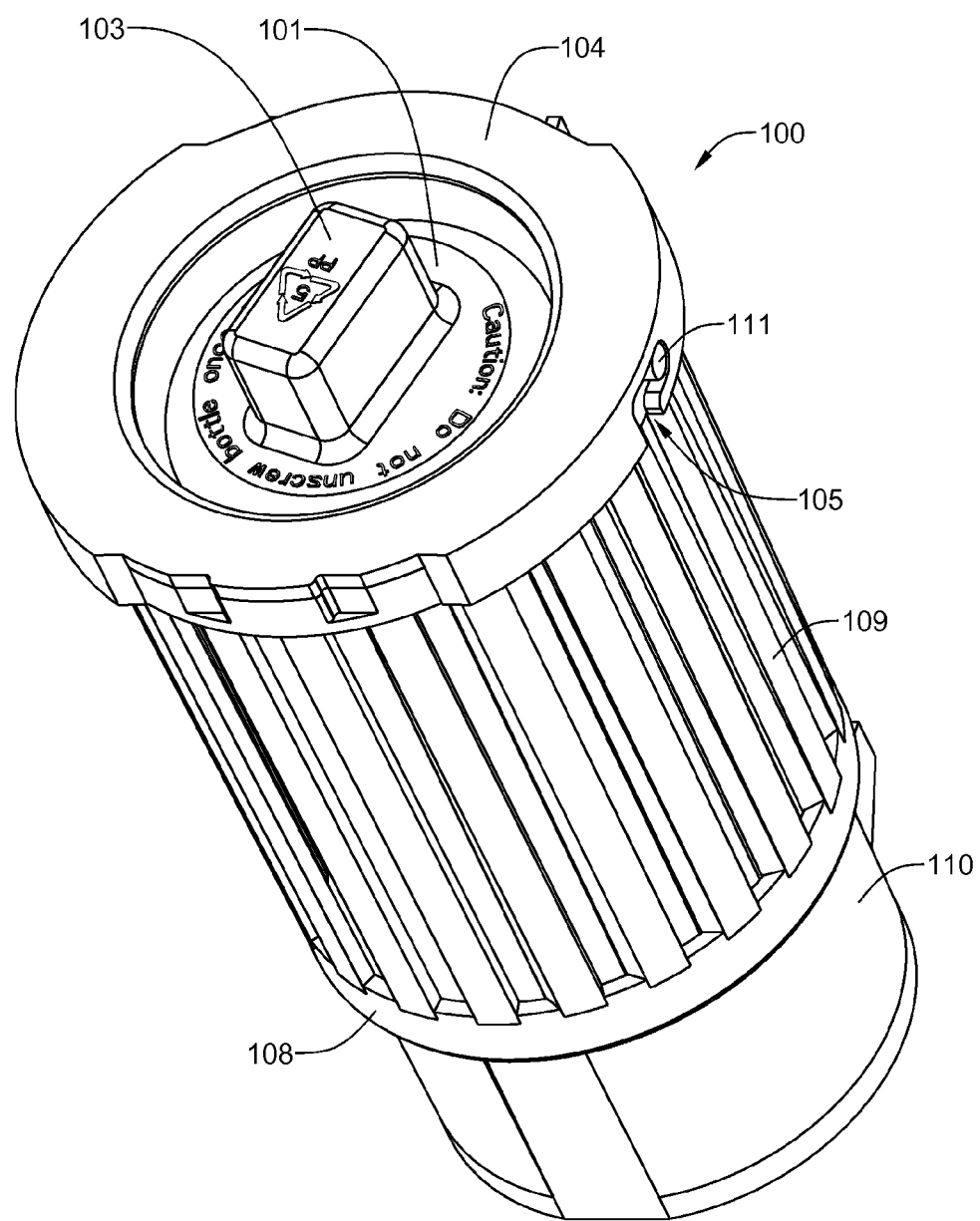
FIG. 2 is first fully-assembled isometric view of the new air freshener canister having a supply vessel installed therein.
Figure 3:
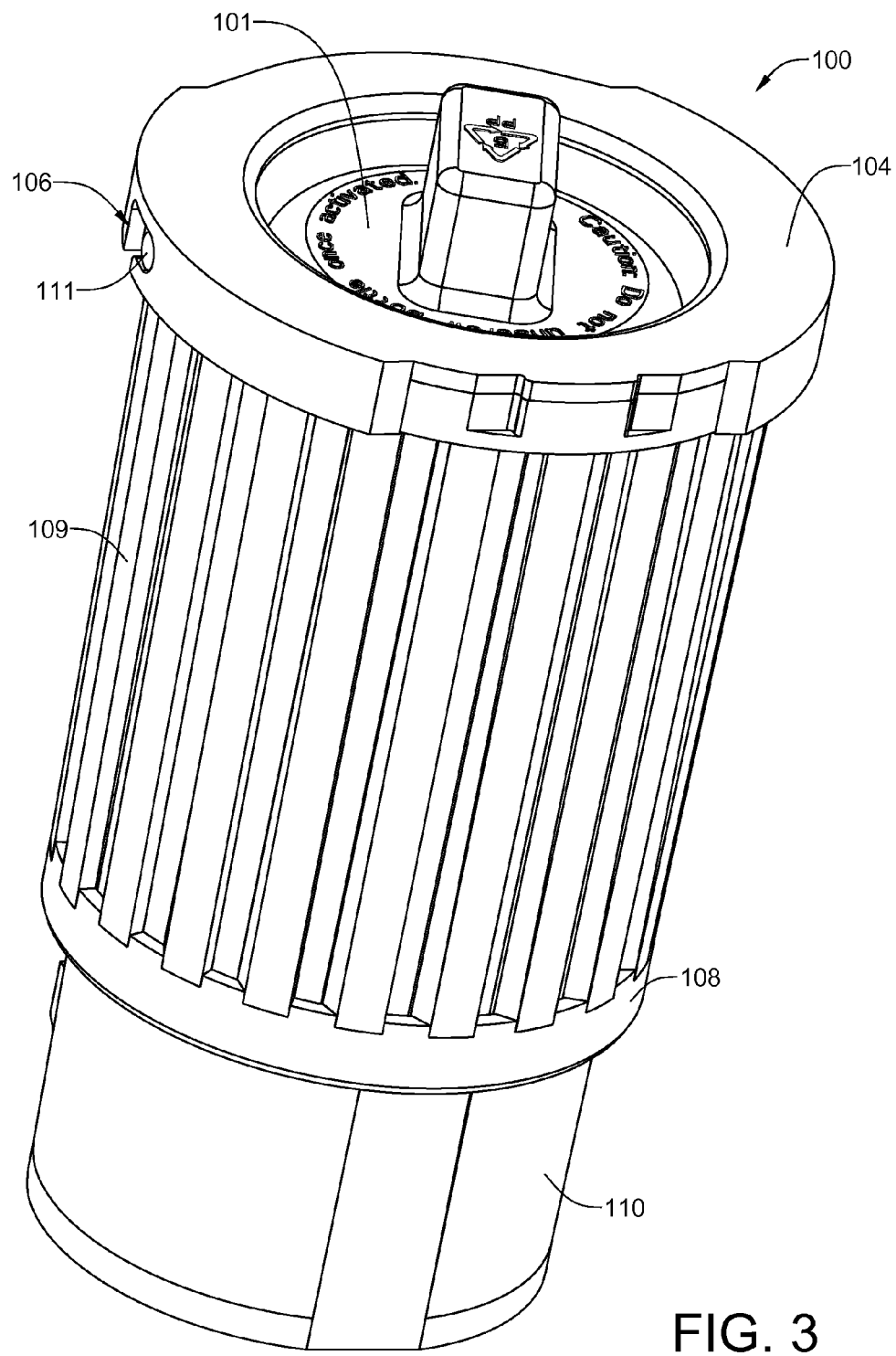
FIG. 3 is a second fully-assembly isometric view of the new air freshener canister having a supply vessel installed therein.
Figure 4:
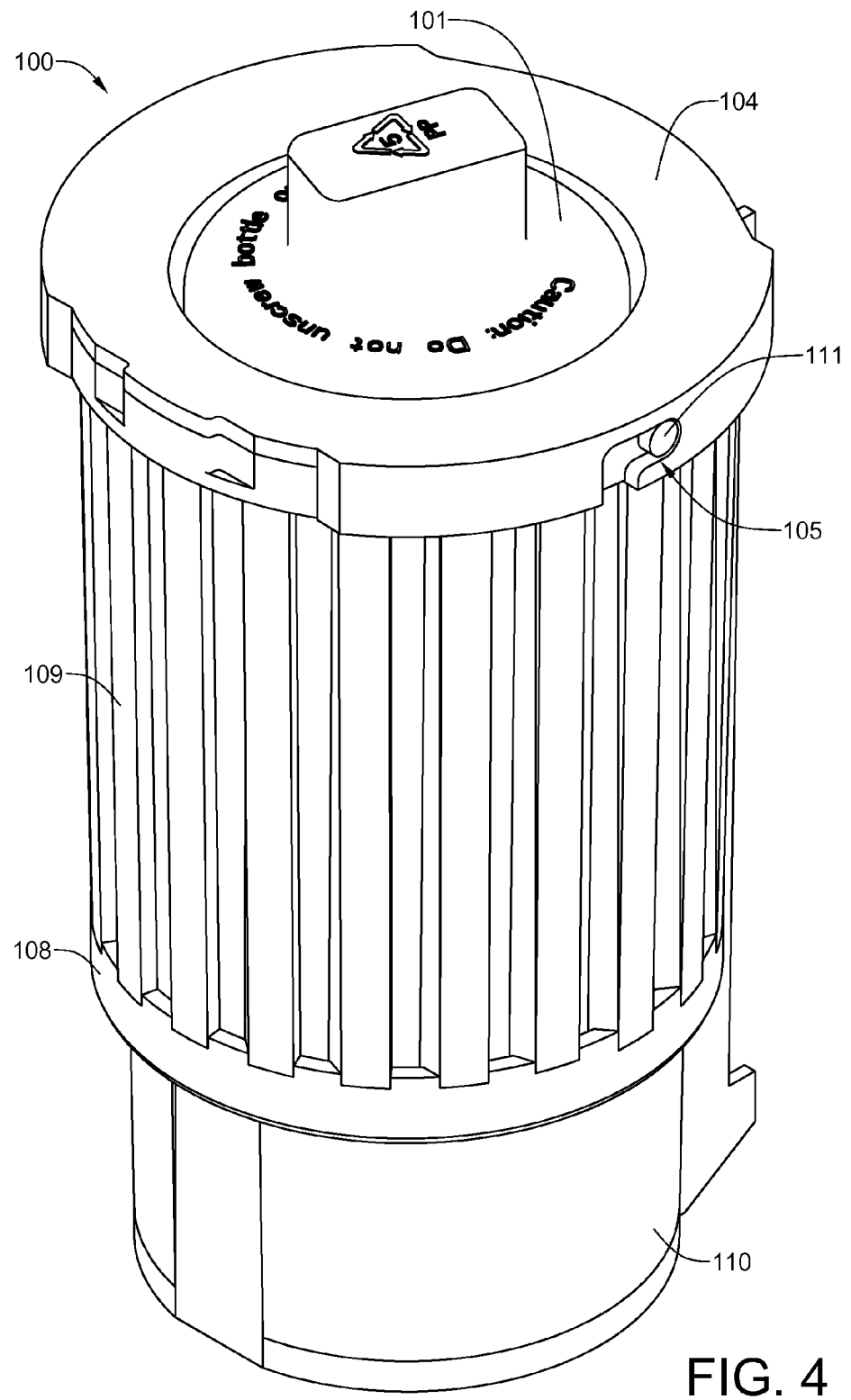
FIG. 4 is a third fully-assembled isometric view of the new air freshener canister having a supply vessel installed therein.
Figure 5:
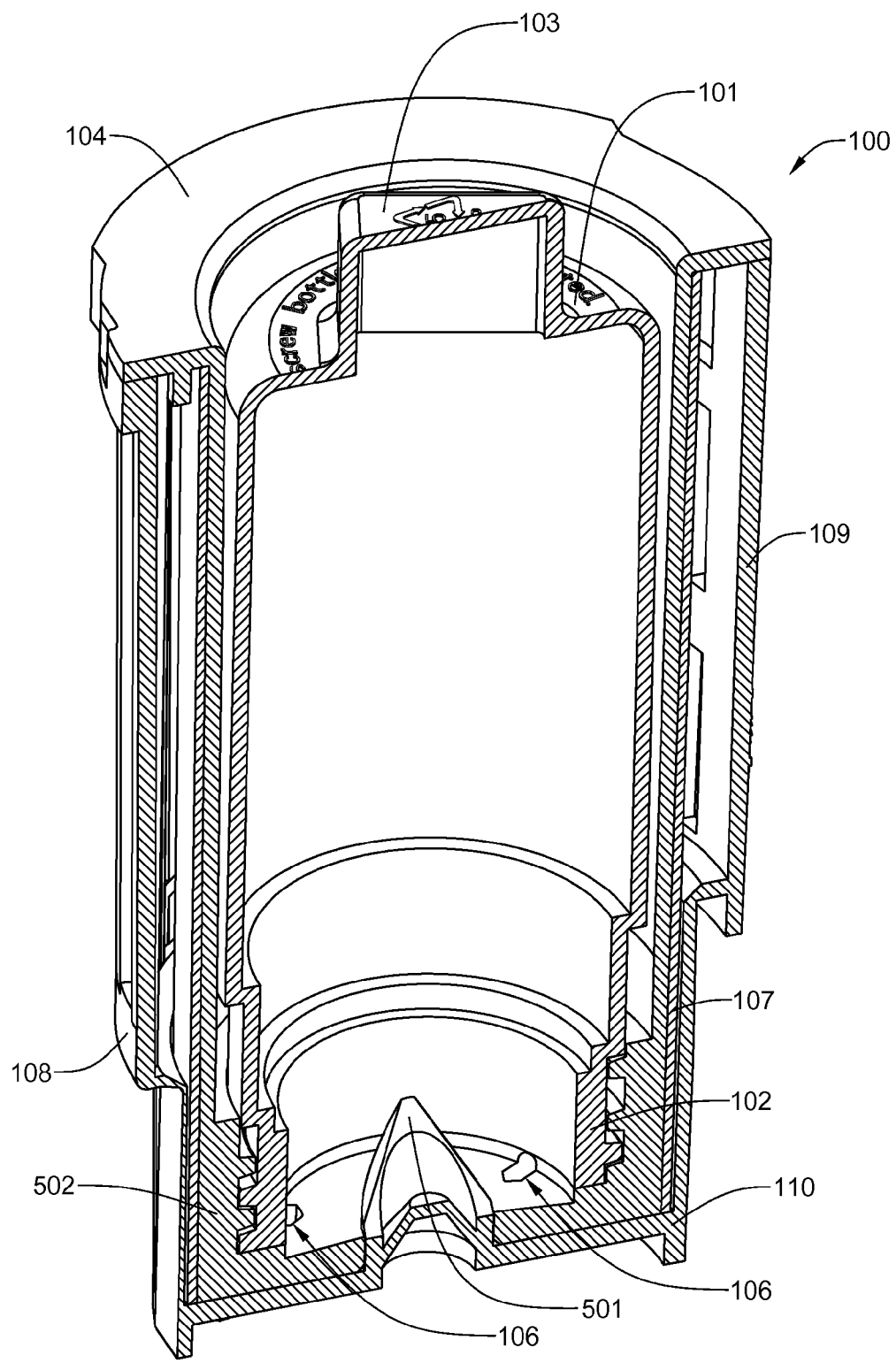
FIG. 5 is a cross-sectional isometric view of the new air freshener canister having a supply vessel installed therein.
Figure 6:
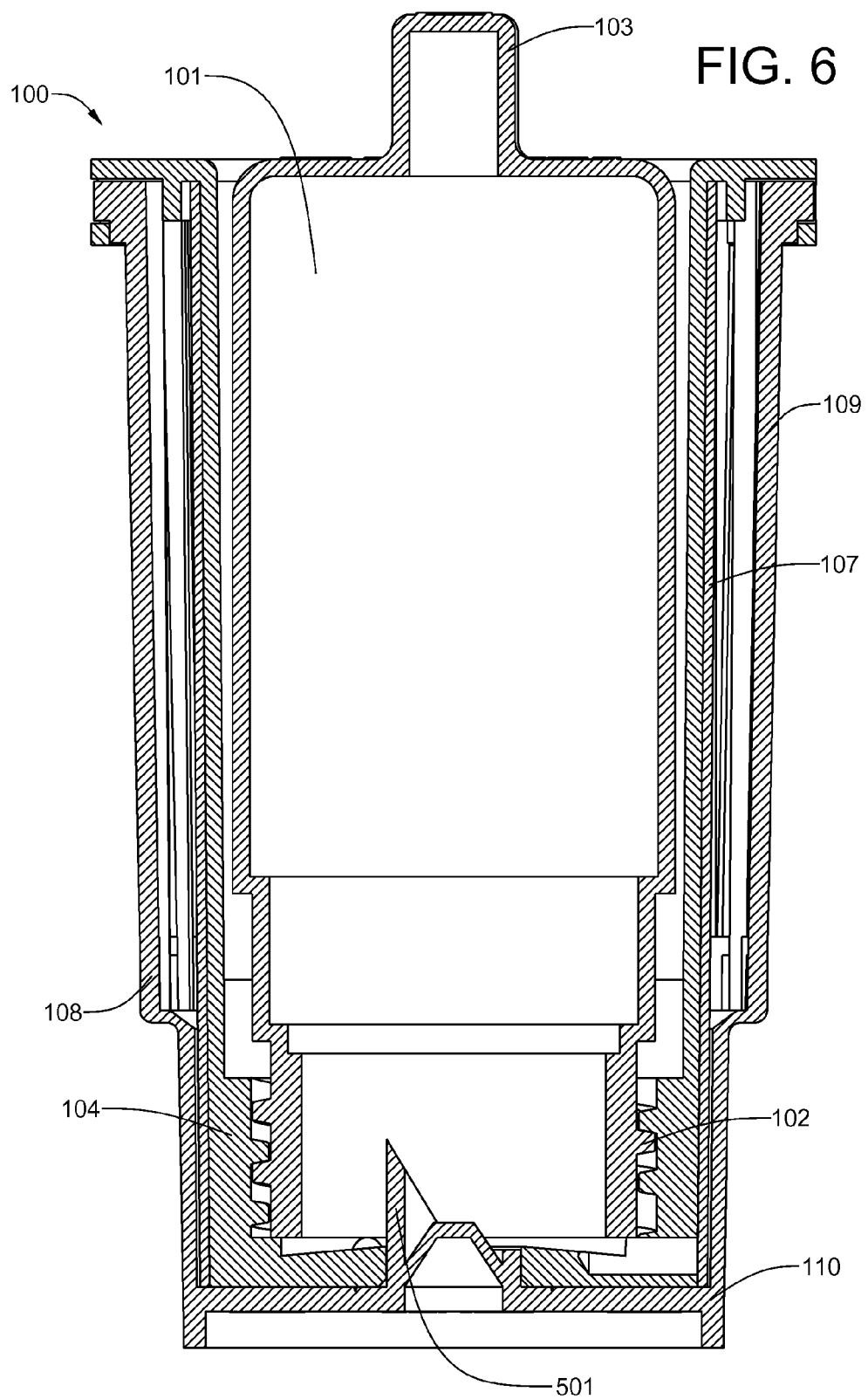
FIG. 6 is an elevational cross-sectional view of the new air freshener canister having a supply vessel installed therein.

The invention will now be described in detail with reference to the attached drawing figures. It is to be understood that the drawings are not necessarily drawn to scale and that they are intended to be merely illustrative.

Referring now to FIGS. 1 through 6, the new spill-resistant air freshener canister 100 is shown in an exploded (disassembled) state. The air freshener canister 100 includes the following components: a supply vessel 101 filled with aromatic liquid that has a finger-twistable projection 103 and a threaded mouth 102 sealed with a puncturable membrane 703; a cylindrical inner sleeve 104 incorporating a socket (see FIG. 5, item 502) that sealably engages the threaded mouth 102 of the supply vessel 101, the cylindrical inner sleeve 104 also having a cylindrical axial aperture at the bottom of the socket, and at least one seepage aperture 106 at the very bottom of the socket which enables liquid from inside the supply vessel to escape in a radially outward direction to the exterior of the cylindrical inner sleeve 104; a cylindrical wick 107 surrounding the cylindrical inner sleeve 104; and an evaporator cage 108 into which the cylindrical inner sleeve 104 is inserted. The evaporator cage 108 includes a bottom portion 110 that may be fully enclosed and may include a central projecting blade (see FIG. 5, item 501) that fits through the axial aperture at the bottom of the socket 502. The evaporator cage 108 also has an open grill work 109 through which evaporating aromatic liquid escapes into the atmosphere. The bottom portion 110 is ultrasonically welded to the bottom of the cylindrical inner sleeve 104, leaving no gap between the bottom of the cylindrical inner sleeve lot and the bottom portion of the evaporator cage 108. When a filled supply vessel 101 is screwed into the socket 502, the projecting blade 501 slices through the puncturable membrane 703, which allows aromatic liquid to escape outside the cylindrical inner sleeve 104 and wet the cylindrical wick 107. The air freshener canister 100 is spill resistant, as there is no unabsorbed standing aromatic liquid outside the supply vessel 101. All of the aromatic liquid is either within the supply vessel 101 or absorbed by the cylindrical wick 107. It will be noted that the cylindrical inner sleeve 104 has locking apertures 105 that fit over projections 111 on the evaporator cage 108.

Figure 7:
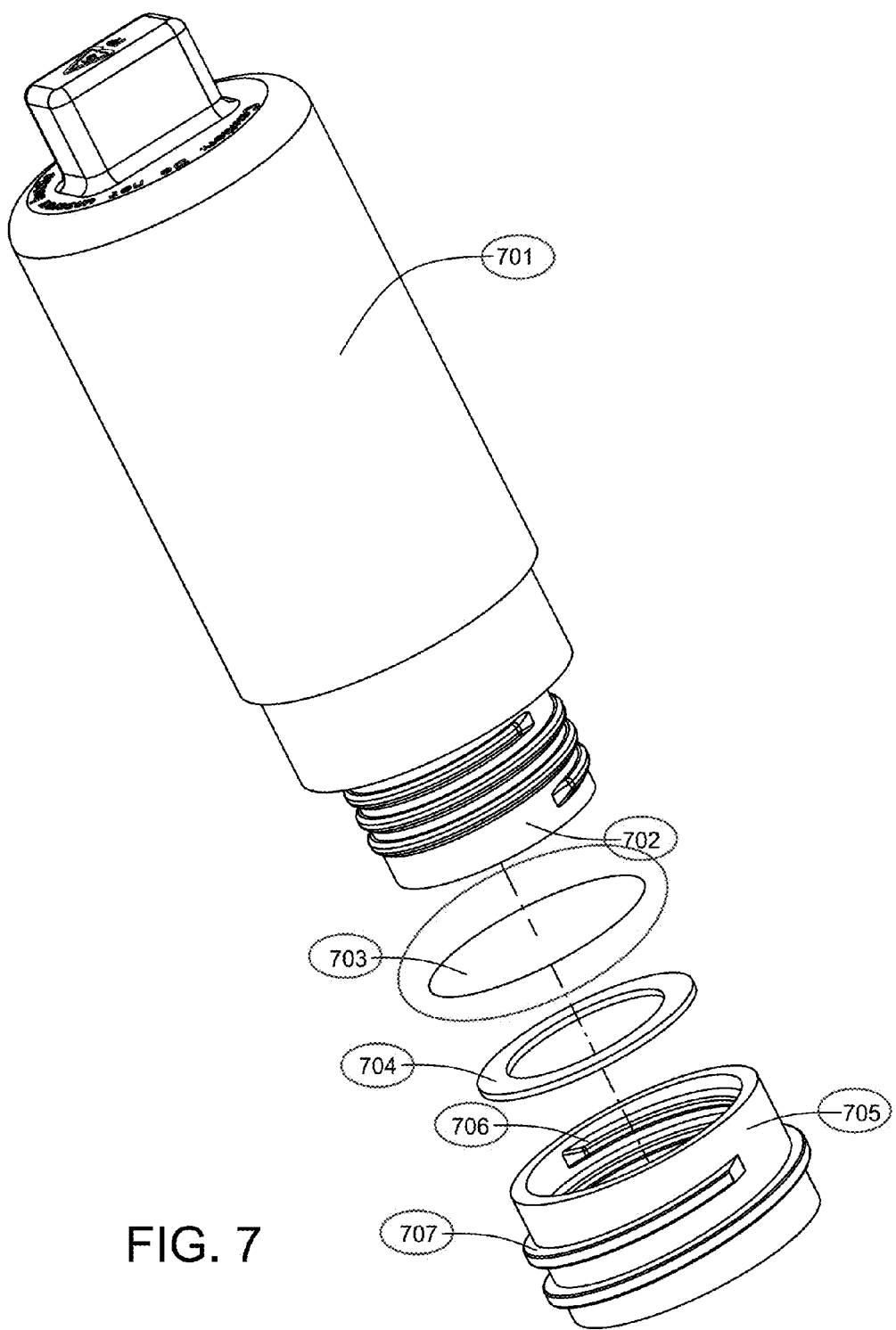
FIG. 7 is an isometric view of a second embodiment supply vessel, a puncturable membrane, a paper washer and a cap having internal and external threads.
Figure 8:
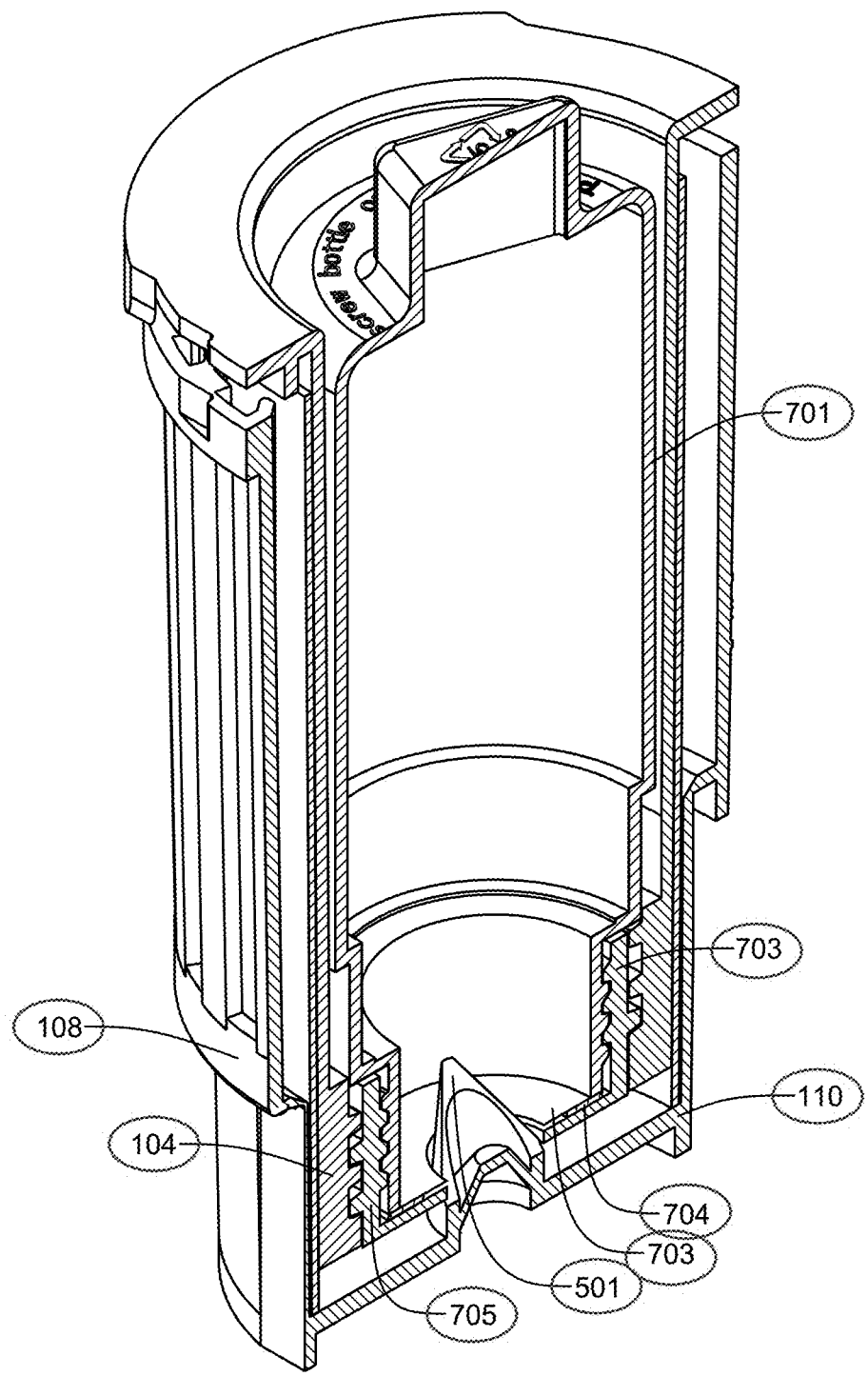
FIG. 8 is a cross sectional view of a second embodiment air freshener canister.

A second embodiment air freshener canister shown in FIGS. 7 and 8 has been designed to improve sealing between the mouth 702 of the supply vessel 701 and the puncturable membrane 703. A supply vessel 701 having an a mouth puncturable 702, a puncturable membrane 703, a paper washer 704, and a cap 705 having internal threads 706 and external threads 707 is shown separately in FIG. 7. The mouth 702 may be externally threaded. The puncturable membrane 703 may comprise polyethylene or foil. The cap 705 fits over the threaded mouth of the supply vessel 701. The paper washer 704 compresses and ensures even force against the polyethylene/foil membrane 703 during inductive sealing of the puncturable membrane to edges of the mouth of the supply vessel.

Although only two embodiments of the new spill-resistant air freshener canister 100 have been shown and described, it will be obvious to those having ordinary skill in the art that changes and modifications may be made thereto without departing from the scope and the spirit of the invention as hereinafter claimed.

What is claimed is:

1. A spill-resistant air freshener canister comprising:
   a supply vessel for holding an aromatic liquid, said supply vessel having a mouth sealed with a puncturable membrane;
   a cylindrical inner sleeve incorporating a socket that sealably engages the mouth of the supply vessel, the cylindrical inner sleeve also having a cylindrical axial aperture at a bottom of the socket, and at least one seepage aperture at a very bottom of the socket which enables liquid from inside the supply vessel to escape in a radially outward direction to the exterior of the cylindrical inner sleeve;
   a cylindrical wick surrounding the cylindrical inner sleeve; and
   an evaporator cage into which the cylindrical inner sleeve is inserted, the evaporator cage having a fully-enclosed interior bottom portion containing a central projecting blade that fits through the cylindrical axial aperture at the bottom of the socket and punctures the puncturable membrane covering the mouth of the supply vessel when the mouth of the supply vessel engages the socket, the fully-enclosed interior bottom portion of the evaporator cage being ultrasonically welded to a bottom portion of the socket of the cylindrical inner sleeve, leaving no gap between the bottom portion of the socket and the fully-enclosed interior bottom portion of the evaporator cage.

2. The spill-resistant air freshener canister of claim 1, which further comprises a cap and a resilient washer, the cap having both internal threads and external threads, wherein the internal threads engage external threads on the mouth of the supply vessel and the external threads of the cap engage internal threads within the socket, the cap enabling the puncturable membrane and the resilient washer to be compressed against the edges of the mouth by tightening the cap on the mouth of the supply vessel, thereby ensuring more even force of the puncturable membrane against edges of the mouth during a process of inductive sealing of the puncturable membrane to the edges of the mouth of the supply vessel.

3. A spill-resistant air freshener canister comprising:
   a supply vessel for holding an aromatic liquid, the supply vessel having a mouth sealed with a puncturable membrane;
   a cylindrical inner sleeve incorporating a socket that sealably engages the mouth of the supply vessel, the cylindrical inner sleeve also having a central projecting blade at a bottom of the socket, and at least one seepage aperture at a very bottom of the socket which enables liquid from inside the supply vessel to escape in a radially outward direction to the exterior of the cylindrical inner sleeve;
   a cylindrical wick surrounding the cylindrical inner sleeve; and
   an evaporator cage into which the cylindrical inner sleeve is inserted, the evaporator cage having a fully-enclosed interior bottom portion that is ultrasonically welded to a bottom portion of the socket of the cylindrical inner sleeve, leaving no gap between the bottom portion of the socket and the fully-enclosed interior bottom portion of the evaporator cage.

4. The spill-resistant air freshener canister of claim 3, which further comprises a cap and a resilient washer, the cap having both internal threads and external threads, wherein the internal threads engage external threads on the mouth of the supply vessel and the external threads of the cap engage internal threads within the socket, the cap enabling the puncturable membrane and the resilient washer to be compressed against the edges of the mouth by tightening the cap on the mouth of the supply vessel, thereby ensuring more even force of the puncturable membrane against the edges of the mouth during a process of inductive sealing of the puncturable membrane to the edges of the mouth of the supply vessel.

* * * * *